US008367602B2

(12) United States Patent
Lyngstadaas et al.

(10) Patent No.: US 8,367,602 B2
(45) Date of Patent: Feb. 5, 2013

(54) CONSENSUS PEPTIDES AND A METHOD FOR INDUCING BIOMINERALIZATION

(75) Inventors: Stale Petter Lyngstadaas, Nesoddtangen (NO); Jan Eirik Ellingsen, Bekkestua (NO)

(73) Assignee: Corticalis AS, Nesoddtangen (NO)

( * ) Notice: Subject to any disclaimer, the term of this patent is extended or adjusted under 35 U.S.C. 154(b) by 65 days.

(21) Appl. No.: 12/520,651

(22) PCT Filed: Dec. 21, 2007

(86) PCT No.: PCT/IB2007/004068
§ 371 (c)(1),
(2), (4) Date: Sep. 4, 2009

(87) PCT Pub. No.: WO2008/078167
PCT Pub. Date: Jul. 3, 2008

(65) Prior Publication Data
US 2010/0172949 A1    Jul. 8, 2010

Related U.S. Application Data

(60) Provisional application No. 60/876,149, filed on Dec. 21, 2006.

(51) Int. Cl.
*A61K 38/00* (2006.01)
*A61P 19/08* (2006.01)
(52) U.S. Cl. ............... 514/1.1; 530/300; 514/16.7
(58) Field of Classification Search ............... None
See application file for complete search history.

(56) References Cited

U.S. PATENT DOCUMENTS 6,274,702 B1    8/2001    Tam
7,132,015 B2    11/2006    Wen et al.

FOREIGN PATENT DOCUMENTS

WO    WO 2006/064381    6/2006
WO    WO 2006/126595    11/2006

OTHER PUBLICATIONS

Bowie et al., 1990, Science 247: 1306-1310.*
Wells, 1990, Biochemistry 29:8509-8517.*
Mickle et al., Med. Clin. North Am., 2000, vol. 84(3), p. 597-607.*
Adelhorst et al., J. Biol. Chem. 269: 6275-6278, 1994.*

Joana Maria Ramis et al., *Synthetic Peptides Analogue to Enamel Proteins Enhance Differentiation of Human Mesenchymal Stem Cells Toward the Osteogenic Lineage*, Not Yet Published (working draft as of Dec. 1, 2011).
Marina Rubert et al., *Synthetic Peptides Analogue to Enamel Proteins Promote Osteogenic Differentiation of MC3T3-E1*, Not Yet Published (working draft as of Dec. 1, 2011).
Database Uniprot [Online], "Q567X6_DANRE," May 10, 2005, XP002482040 (Abstract).
Itoh et al., "Enhancement of osteogenesis on hydroxyaptite surface coated with synthetic peptide (EEEEEEEPRGDT) in vitro," *Journal of Biomedical Material Research*, 2002, vol. 62, pp. 292-298, XP002482039, Wiley Periodicals, Inc.
Zou et al., "Determination of protein regions responsible for interactions of amelogenin with CD63 and MLAMP1," *Biochemical Journal*, Dec. 15, 2007, vol. 408, No. 3, pp. 347-354, XP008092160, The Authors Journal Compilation.
Ronold et al., "The use of a coin shaped implant for direct in situ measurement of attachment strength for osseointegrating biomaterial surfaces," *Biomaterials*, 2002, vol. 23, pp. 2201-2209, Elsevier Science Ltd.
Svensson et al., "Histidine tag fusion increases expression levels of active recombinant amelogenin in *Escherichia coli*," *Protein Expression & Purification*, 2006, vol. 48, pp. 134-141, Elsevier Inc.
Hayakawa, "Direct attachment of fibronectin to tresyl chloride-activated titanium," *Journal of Biomedical Materials Research*, 2003, vol. 67A, No. 2, pp. 684-688, Wiley Periodicals, Inc.
Imamura et al., "Adsorption Characteristics of Oligopeptides Composed of Acidic and Basic Amino Acids on Titanium Surface," *Journal of Bioscience and Bioengineering*, 2007, vol. 103, No. 1, pp. 7-12, The Society for Biotechnology, Japan.
Lian et al., "Runx2/Cbfa1: A Multifunctional Regulator of Bone Formation," *Current Pharmaceutical Design*, 2003, vol. 9, pp. 2677-2685, Bentham Science Publishers Ltd.
Messieh, "Levels of Lactate Dehydrogenase in Osteoarthritic and Failed Total Knee Joints," The Journal of Arthoplasty, 1996, vol. 11, No. 3, pp. 354-355, Aspen Medical Group, St. Paul, Minnesota.
Messieh, "Synovial Fluid Levels of Lactate Dehydrogenase in Patients With Total Knee Arthroplasty," The Journal of Arthoplasty, 1996, vol. 11, No. 4, pp. 484-486, Aspen Medical Group, St. Paul, Minnesota.
Minkim et al., "Role of the Osteoclast at the None-Implant Interface," Adv Dent Res, Jun. 1999, vol. 13, pp. 49-56, Sage Publications.

* cited by examiner

*Primary Examiner* — Gyan Chandra
(74) *Attorney, Agent, or Firm* — Buchanan Ingersoll & Rooney PC

(57) ABSTRACT

The present invention relates to artificial peptides optimized for the induction and/or stimulation of mineralization and/or biomineralization. The invention also relates to the use of these artificial peptides for the induction and/or stimulation of mineralization and/or biomineralization in vivo and in vitro.

18 Claims, 5 Drawing Sheets

SEQUENCE LISTING

<160> NUMBER OF SEQ ID NOS: 8

<210> SEQ ID NO 1
<211> LENGTH: 92
<212> TYPE: PRT
<213> ORGANISM: Artificial Sequence
<220> FEATURE:
<223> OTHER INFORMATION: Consensus peptide
<221> NAME/KEY: VARIANT
<222> LOCATION: (1)...(92)
<223> OTHER INFORMATION: Positions 2-3, 9-10, 15-16, 18, 34-35, 37,
      48-49, 56-57, 62-63, 68-69, 74, 77-84, 86-87, 89-92 may
      independently be selected from Ala, Ile, Leu, Met,
      Phe, Trp and Val
<221> NAME/KEY: VARIANT
<222> LOCATION: (1)...(92)
<223> OTHER INFORMATION: Positions 5-7, 12-13, 20-25, 27-32, 39-41,
      43-44, 46, 51, 53-54, 59-60, 65-66, 71 may independently
      be selected from Asn, Cys, Gln, Ser, Thr and Tyr

<400> SEQUENCE: 1

Pro Xaa Xaa Pro Xaa Xaa Xaa Pro Xaa Xaa Pro Xaa Xaa Pro Xaa Xaa
 1               5                   10                  15

Pro Xaa Pro Xaa Xaa Xaa Xaa Xaa Pro Xaa Xaa Xaa Xaa Xaa Xaa Xaa
            20                  25                  30

Pro Xaa Xaa Pro Xaa Pro Xaa Xaa Pro Xaa Xaa Pro Xaa Pro Xaa
        35                  40                  45

Xaa Pro Xaa Pro Xaa Xaa Pro Xaa Xaa Pro Xaa Xaa Pro Xaa Xaa Pro
    50                  55                  60

Xaa Xaa Pro Xaa Xaa Pro Xaa Pro Pro Xaa Pro Pro Xaa Xaa Xaa Xaa
65                  70                  75                  80

Xaa Xaa Xaa Xaa Pro Xaa Xaa Pro Xaa Xaa Xaa Xaa
                85                  90

<210> SEQ ID NO 2
<211> LENGTH: 25
<212> TYPE: PRT
<213> ORGANISM: Artificial Sequence
<220> FEATURE:
<223> OTHER INFORMATION: Consensus peptide
<221> NAME/KEY: VARIANT
<222> LOCATION: (1)...(25)
<223> OTHER INFORMATION: Positions 2-3, 8-9, 14-15, 23 may
      independently be selected from Ala, Ile, Leu, Met, Phe, Trp and
      Val
<221> NAME/KEY: VARIANT
<222> LOCATION: (1)...(25)
<223> OTHER INFORMATION: Positions 5-6, 11-12, 17-18, 20 may
      independently be selected from Asn, Cys, Gln, Ser, Thr and Tyr

<400> SEQUENCE: 2

Pro Xaa Xaa Pro Xaa Xaa Pro Xaa Xaa Pro Xaa Xaa Pro Xaa Xaa Pro
 1               5                   10                  15

Xaa Xaa Pro Xaa Pro Pro Xaa Pro Pro
            20                  25

<210> SEQ ID NO 3
<211> LENGTH: 25
<212> TYPE: PRT
<213> ORGANISM: Artificial Sequence
<220> FEATURE:
<223> OTHER INFORMATION: Mineralization/biomineralization inducing
      peptide

<400> SEQUENCE: 3

Pro Leu Val Pro Ser Tyr Pro Leu Val Pro Ser Tyr Pro Leu Val Pro

```
                1               5                   10                  15
Ser Tyr Pro Tyr Pro Pro Leu Pro Pro
                20                  25

<210> SEQ ID NO 4
<211> LENGTH: 25
<212> TYPE: PRT
<213> ORGANISM: Artificial Sequence
<220> FEATURE:
<223> OTHER INFORMATION: Mineralization/biomineralization inducing
      peptide

<400> SEQUENCE: 4

Pro Leu Val Pro Ser Gln Pro Leu Val Pro Ser Gln Pro Leu Val Pro
1               5                   10                  15

Ser Gln Pro Gln Pro Pro Leu Pro Pro
                20                  25

<210> SEQ ID NO 5
<211> LENGTH: 25
<212> TYPE: PRT
<213> ORGANISM: Artificial Sequence
<220> FEATURE:
<223> OTHER INFORMATION: Mineralization/biomineralization inducing
      peptide

<400> SEQUENCE: 5

Pro Leu Val Pro Cys Cys Pro Leu Val Pro Cys Cys Pro Leu Val Pro
1               5                   10                  15

Cys Cys Pro Cys Pro Pro Leu Pro Pro
                20                  25

<210> SEQ ID NO 6
<211> LENGTH: 25
<212> TYPE: PRT
<213> ORGANISM: Artificial Sequence
<220> FEATURE:
<223> OTHER INFORMATION: Mineralization/biomineralization inducing
      peptide

<400> SEQUENCE: 6

Pro Met Met Pro Ser Tyr Pro Met Met Pro Ser Tyr Pro Met Met Pro
1               5                   10                  15

Ser Tyr Pro Tyr Pro Pro Met Pro Pro
                20                  25

<210> SEQ ID NO 7
<211> LENGTH: 25
<212> TYPE: PRT
<213> ORGANISM: Artificial Sequence
<220> FEATURE:
<223> OTHER INFORMATION: Mineralization/biomineralization inducing
      peptide

<400> SEQUENCE: 7

Pro Leu Val Pro Ser Ser Pro Leu Val Pro Ser Ser Pro Leu Val Pro
1               5                   10                  15

Ser Ser Pro Ser Pro Pro Leu Pro Pro
                20                  25

<210> SEQ ID NO 8
<211> LENGTH: 25
<212> TYPE: PRT
<213> ORGANISM: Artificial Sequence
<220> FEATURE:
<223> OTHER INFORMATION: Mineralization/biomineralization inducing
```

```
                        peptide

<400> SEQUENCE: 8

Pro Leu Val Pro Ser Ser Pro Leu Val Pro Cys Cys Pro Leu Val Pro
 1               5                   10                  15

Cys Cys Pro Ser Pro Pro Leu Pro Pro
            20              25
```

CONSENSUS PEPTIDES AND A METHOD FOR INDUCING BIOMINERALIZATION

TECHNICAL FIELD

The present invention relates to the field of induction and/or stimulation of mineral precipitation and/or biomineralization and artificial peptides able to induce and/or stimulate mineral precipitation and/or biomineralization clinically, industrially and/or chemically.

BACKGROUND ART

The hard tissues of organisms, e.g. teeth, bone, mollusk shells etc. are composed of minerals often in association with an organic polymeric phase.

Biomineralization is the process by which mineral deposits within or outside cells of different organisms form the above described structures. Examples of minerals deposited include iron, gold, silicates, calcium carbonate and calcium phosphate. The cells themselves direct the process of biomineralization e.g. by the expression of proteins that act as nucleators and the production of enzymes that modify the functions of such proteins. Most proteins associated with biomineralization are anionic which allows them to interact with the charged mineral crystal surfaces.

Biomimetics is defined as microstructural processing techniques that mimics or are inspired by the natural way of producing minerals, such as apatites. The means by which organisms use organic substances to grow mineral is of interest in biomimetics. For example the mineral deposition properties of biopolymers and synthetic analogoues thereof have been utilized in industrial processes, e.g. in water treatment and in electronic devices. Many man-made crystals require elevated temperatures and strong chemical solutions whereas the organisms have long been able to lay down elaborate mineral structures at ambient temperatures. Often the mineral phases are not pure but are made as composites which entail an organic part, often protein, which takes part in and controls the biomineralization. These composites are often not only as hard as the pure mineral but also tougher, as at last, the micro-environment controls biomineralization. There is therefore a great interest in the utilization of biopolymers for industrial applications to induce mineral precipitation.

Also it is of great interest to utilize biopolymers in biological systems for various purposes. One such example is in medical prosthetic device technology. Bone medical prosthetic devices made of metal or metal alloys are commonly used. Some of the metals and alloys used for bone medical prosthetic devices, such as titanium, zirconium, hafnium, tantalum, niobium or alloys thereof, may form a strong bond with bone tissue. This bonding between the metal and bone tissue has been termed "osseointegration" (Brånemark et al. "Osseointegrated medical prosthetic devices in the treatment of the edentulous jaw, Experience from a 10-year period", Almqvist & Wiksell International, Stockholm, Sweden). When implanted into a subject, bone tissue grows onto the medical prosthetic device surfaces so that the medical prosthetic device is attached to bone tissue. However, this is a slow process under which the medical prosthetic device often may not be loaded. Therefore, it would be valuable to improve the rate at which medical prosthetic devices attach to bone.

It is also of great interest to develop methods for the regeneration of mineralized tissue, such as bone, e.g. after trauma, surgical removal of bone or teeth or in connection with cancer therapy.

A number of natural peptides have been shown to induce mineral precipitation. Examples include collagen 1 and 2, amelogenins, ameloblastin, bone sialoprotein, enamelin, and ansocalcin. However, it is not always practical to use natural proteins for the purpose of inducing mineral precipitation and/or biomineralization. For example, natural proteins are often long, which means they are difficult to synthesize, both chemically and by bioproduction. A natural protein only contains natural amino acids, and may therefore be susceptible to rapid degradation. Also, if purified from a natural environment, such as developing teeth, there is always a risk of contamination of other products which e.g. may cause allergic reactions. In addition, a long natural protein normally has many roles in a living body and may therefore not be optimized for the induction and stimulation of mineralization.

It is therefore of great interest to develop peptides and methods which allow for an improved mineralization in vitro and in vivo.

SUMMARY OF INVENTION

It is therefore an object of the present invention to provide an artificial peptide with improved properties for induction and/or stimulation of mineralization, in vivo and in vitro.

It is a further object to provide such a peptide which is easier to synthesize than natural proteins and to provide methods of using the peptides of the invention for the induction and/or stimulation of mineral precipitation and/or biomineralization.

The above defined objects are in a first aspect of the invention achieved by providing an artificial peptide according to any of SEQ ID NO 1-8.

In another aspect, the above identified objects are achieved by providing a pharmaceutical composition comprising one or more of the peptides of SEQ ID NO 1-8.

In another aspect, the invention relates to the use of the peptides of the invention for the induction and/or stimulation of mineralization and/or biomineralization.

Yet other aspects of the invention relates to a surface having a peptide of the invention provided thereon, and methods for providing such surfaces.

The invention also relates to the in vivo induction and/or stimulation of biomineralization, as well as to the regeneration of bone.

Since the amino acid sequences of the artificial peptides of SEQ ID NO 1-8 have been selected based on their mineralization inducing and/or stimulating activities, they have an improved activity in inducing and/or stimulating mineralization as compared to peptides available in the art. Further, due to their shorter length compared to natural mineralization inducing proteins, the artificial peptides of the invention are easier to synthesize.

DEFINITIONS

Figure 1:
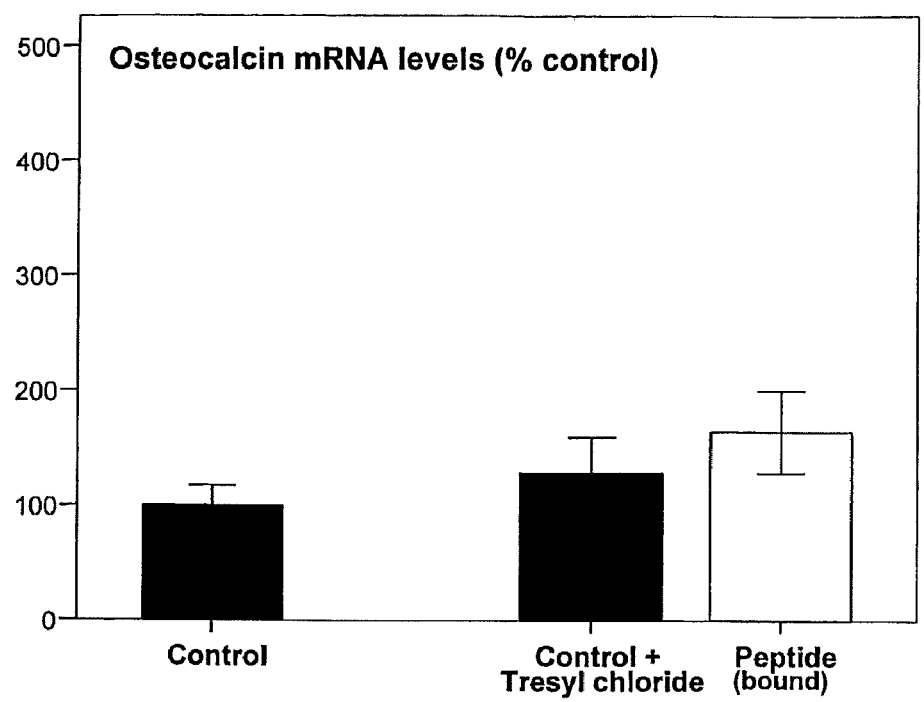
FIG. 1. Osteocalcin gene expression in the peri-implant bone tissue attached to the modified titanium implants (Example 5).

"Precipitation of mineral" or "mineral precipitation" relates to the in vivo and in vitro formation of structures comprising calcium and phosphate in, but not limited to, e.g. solutions, onto surfaces, in tissues, and on medical prosthetic devices etc. Examples of structures comprising calcium and phosphate include, but are not limited to, all kinds of bone, cartilage, all kinds of dentin, cementum, enamel, calculus, hair, nails, ligament, beaks, dermal scales etc.

"Biomineralization" relates to the production of partly or wholly mineralized internal or external structures by living organisms. In the present context, the term "biomineralization" embraces the formation, maturation and remodelling of bone, cartilage, cementum and dental tissues.

In the present context, an "artificial peptide" refers to a peptide that is a non-natural peptide in the sense that it does not normally occur in nature but is the product of amino acids put together and selected in an order, amount and manner generating peptides suitable for use in the context of the present invention. An "artificial peptide" is still a peptide embraced by the present invention even though it might encompass parts of or a whole peptide which happens to be present in nature. "Artificial" may be used interchangeably with terms such as "synthetic" or "non-natural".

In the present context "Pro" denotes the amino acid proline.

In the present context "X" denotes a hydrophobic amino acid. A hydrophobic amino acid is, in the present context, defined as an amino acid selected from the group consisting of: Ala, Ile, Leu, Met, Phe, Trp and Val.

In the present context "Y" denotes a polar amino acid. A polar ("hydrophilic") amino acid is, in the present context, defined as an amino acid selected from the group consisting of: Asn, Cys, Gln, Ser, Thr and Tyr.

In the present context, common nomenclature is used for denoting amino acids. Therefore, for example, A is Ala (hydrophobic), C is Cys (polar), F is Phe (hydrophobic), H is His, I is Ile (hydrophobic), L is Leu (hydrophobic), M is Met (hydrophobic), N is Asn (polar), Q is Gln (polar), S is Ser (polar), T is Thr (polar), V is Val (hydrophobic), W is Trp (hydrophobic), Y is Tyr (polar).

"Medical prosthetic device" in the present context refers to any device intended to be implanted into the body of a vertebrate animal, such as a mammal, e.g. a human mammal. Medical prosthetic devices in the present context may be used to replace anatomy and/or restore any function of the body. Examples of medical prosthetic devices include, but are not limited to, dental implants and orthopedic implants.

In the present context "surface" refers to any surface which may be of interest to provide with an artificial peptide of the invention, such as a metal surface, e.g. a titanium, zirconium, tantalum, aluminium, gold, surgical steel or a nickel surface, or an alloy thereof, or a metal oxide surface thereof, or a metal hydroxide or metal hydride surface thereof, or a hydroxyl apatite, aragonite, bioglass, glass, or polyurethane surface. Another example of a surface according to the invention includes a medical prosthetic device surface, such as a metallic, metal oxide, or a polymeric medical prosthetic device surface. Another example of a surface according to the invention is a biological surface, such as a tooth root surface, a dental enamel surface, a bone surface, a graft surface, a wound surface etc. Additional examples of surfaces comprise mucosal surfaces, skin surfaces, articular surfaces of joints, hair and nails and other equivalent surfaces.

In the present context "subject" relate to any vertebrate animal, such as bird, reptiles, mammals, primates and humans.

DETAILED DESCRIPTION OF INVENTION

The present invention relates to artificial peptides as disclosed herein, and their use for the induction and/or stimulation of mineral precipitation and/or biomineralization e.g. onto surfaces, in tissues/or and in a solution, for the formation and/or regeneration of bone as well as for the fusion of two mineralised structures, such as two biomineralized structures or one biomineralized structure and an implantable biomaterial.

In a first aspect the invention relates to an artificial peptide comprising a consensus amino acid sequence being at least 80% identical to the sequence of Pro-X-X-Pro-Y-Y-Y-Pro-X-X-Pro-Y-Y-Pro-X-X-Pro-X-Pro-Y-Y-Y-Y-Y-Pro-Y-Y-Y-Y-Y-Y-Pro-X-X-Pro-X-Pro-Y-Y-Y-Pro-Y-Y-Pro-Y-Pro-X-X-Pro-Y-Pro-Y-Y-Pro-X-X-Pro-Y-Y-Pro-X-X-Pro-Y-Y-Pro-X-X-Pro-Y-Pro-Pro-X-Pro-Pro-X-X-X-X-X-X-X-Pro-X-X-Pro-X-X-X-X (SEQ ID NO 1), wherein a) Pro is proline;
b) X is an amino acid selected from the group consisting of Ala, Ile, Leu, Met, Phe, Trp and Val, preferably Ile, Leu, Val and Met;
c) Y is an amino acid selected from the group consisting of Asn, Cys, Gln, Ser, Thr and Tyr, preferably Ser and Gln.

By a peptide having an amino acid sequence at least, for example 95% identical to a reference amino acid sequence, is intended that the amino acid sequence of the peptide is identical to the reference sequence except that the amino acid sequence may include up to 5 point mutations per each 100 amino acids of the reference amino acid sequence. In other words, to obtain a peptide having an amino acid sequence at least 95% identical to a reference amino acid sequence: up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

Furthermore, the peptides according to the invention may comprise between 20 and 120 amino acids, such as, but not limited to, between 20-25, 25-30, 30-35, 35-40, 40-45, 45-50, 50-60, 60-70, 70-80, 80-90, 90-100, or between 100-120 amino acids, such as, but not limited to, 21, 22, 23, 24, 26, 27, 28, 29, 30, 32, 33, 37, 42, 47, 49, 51, 53, 57, 59, 63, 65, 75, 85, 87, 88, 92, 95, 105, or 115 amino acids. In a preferred embodiment, the peptides according to the invention comprises between 20-50 amino acids.

In the present invention, a local algorithm program is best suited to determine identity. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Another preferred example is Clustal W. Each sequence analysis program has a default scoring matrix and default gap penalties. In general, a molecular biologist would be expected to use the default settings established by the software program used.

The amino acids in an artificial peptide of the invention may further be modified in terms of chemistry, isometry or in any other way as long as the sequences of the peptides are intact. Modifications of the amino acids of the artificial peptides of the invention may increase the activity, stability, biocompatibility or clinical performance of the peptides, or reduce toxicity and adverse reactions to the peptides. Examples of chemical modifications include, but are not limited to, glycosylation and methylation. The amino acids may also be of all different types of stereoisomeric forms, such as D or L forms of amino acids, or S or R isomers. The amino acids in an artificial peptide of the invention may also be replaced by synthetic analogues thereof. The use of synthetic analogues may e.g. result in a peptide that is more stable and less prone to degradation. Examples of unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-a-amino butyric acid*, L-g-amino butyric acid*, L-a-amino isobutyric acid*, L-e-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * is herein utilised to indicate the hydrophobic nature of the derivative whereas # is utilised to indicate the hydrophilic nature of the derivative, #* indicates amphipathic characteristics.

Preferably, an artificial peptide according to the invention comprises an amino acid sequence as shown in SEQ ID NO 1. More preferably, the invention relates to an artificial peptide consisting of an amino acid sequence as shown in SEQ ID NO 1.

The above identified SEQ ID NO 1 is an artificial (synthetic) peptide comprising a poly-proline consensus sequence, further comprising hydrophobic ("X") and polar amino acids ("Y"). This artificial consensus peptide was constructed on the basis of sequence similarities between regions in proteins and peptides that are involved in biomineralization (bone, cartilage, enamel, dentin and cementum formation) in order to obtain a peptide that induce and/or stimulate mineral precipitation in biological systems (biomineralization), and that also may be used clinically, industrially, chemically or otherwise to stimulate the formation of calcium phosphate based structures in tissues, on medical prosthetic devices, onto surfaces, in solutions etc. The protein sequences used for constructing the artificial peptide included the sequences for collagen 1 and 2 (human, mouse and rat), amelogenin (human, mouse, rat, rabbit, pig and cow), ameloblastin (human, rat), bone sialoprotein (human, mouse), enamelin (human, mouse). The artificial peptides of the invention are particularly suitable for the induction and/or stimulation of mineral precipitation and/or biomineralization, as the amino acid sequences are optimised for this purpose. The use of an artificial peptide according to the invention is advantageous due to its shorter length compared to natural peptides, which facilitates the synthesis thereof and allows for the use of amino acid analogues as explained herein. Also, the use of an artificial peptide allows modifications of the amino acid sequence to enable the peptides to bind to e.g. metal surfaces or being easily purified, such as by the choice of amino acid sequence of the peptide itself or the use of N- and/or C-terminal tags.

Therefore, in one aspect, the present invention relates to an artificial peptide comprising an amino acid sequence being at least 80% identical to SEQ ID NO 1, which is able to induce and/or stimulate mineral precipitation and/or biomineralization. Preferably, such an artificial peptide which is able to induce and/or stimulate mineral precipitation and/or biomineralization comprises an amino acid sequence as shown in SEQ ID NO 1, and more preferably such an artificial peptide consists of an amino acid sequence as shown in SEQ ID NO 1.

One further embodiment of the invention relates to a shorter consensus peptide sequence comprising an amino acid sequence being at least 80% identical to the sequence of Pro-X-X-Pro-Y-Y-Pro-X-X-Pro-Y-Y-Pro-X-X-Pro-Y-Y-Pro-Y-Pro-Pro-X-Pro-Pro (SEQ ID NO 2), wherein
a) Pro is proline;
b) X is an amino acid selected from the group consisting of Ala, Ile, Leu, Met, Phe, Trp and Val, preferably Ile, Leu, Val and Met;
c) Y is an amino acid selected from the group consisting of Asn, Cys, Gln, Ser, Thr and Tyr, preferably Ser and Gln.

SEQ ID NO 2 is constructed by the assembly of amino acids 47-50, 53-66 and 70-76 of SEQ ID NO 1, i.e. amino acids underlined in SEQ ID NO 1 above. One preferred embodiment of the invention relates to an artificial peptide comprising an amino acid sequence as shown in SEQ ID NO 2, more preferably consisting of an amino acid sequence as shown in SEQ ID NO 2. Another preferred embodiment relates to an artificial peptide comprising an amino acid sequence being at least 80% identical to SEQ ID NO 2, which is able to induce and/or stimulate mineral precipitation and/or biomineralization. Another preferred embodiment relates to an artificial peptide comprising an amino acid sequence as shown in SEQ ID NO 2, even more preferably consisting of an amino acid sequence as shown in SEQ ID NO 2, which is able to induce and/or stimulate mineral precipitation and/or biomineralization. Due to its short length, SEQ ID NO 2 is advantageous for synthetic production.

The invention also relates to other artificial peptides with a specified amino acid sequence comprised in a consensus sequence of the invention. In a first aspect, such an artificial peptide is PLV PSY PLV PSY PLV PSY PYP PLPP (SEQ ID NO 3). Another preferred amino acid sequence is PLV PSQ PLV PSQ PLV PSQ PQP PLPP (SEQ ID NO 4). These two sequences are the two sequences of the invention that represent the most conserved sequences.

Another aspect of the invention relates to a mineral precipitation and/or biomineralization inducing/stimulating metal binding artificial peptide comprising the amino acid sequence of PLV PCC PLV PCC PLV PCC PCP PLPP (SEQ ID NO 5) or PMM PSY PMM PSY PMM PSY PYP PMPP (SEQ ID NO 6). These two peptides have a high metal binding activity due to their content of amino acids comprising a sulphur atom, e.g. methionine and cysteine. Such amino acids may form a sulfur bridges that may interact directly with a metal surface. The property of metal binding may be of importance when it is desirable to bind a peptide to a metal surface, such as a medical prosthetic device surface, in vivo or in vitro.

Another aspect of the invention relates to an artificial peptide optimized for bone formation stimulation and/or induction comprising the amino acid sequence PLV PSS PLV PSS PLV PSS PSP PLPP (SEQ ID NO 7). This peptide comprises several Ser residues. Ser is well known to act as a signal molecule for bone formation. When a peptide according to SEQ ID NO 7 is digested, processed and/or released from a surface, it is believed that Ser will be released and act as a stimulator of bone formation.

Yet another preferred embodiment of the invention relates to an artificial peptide comprising the amino acid sequence PLV PSS PLV PCC PLV PCC PSP PLPP (SEQ ID NO 8). This peptide is optimized for binding to metal surfaces, induction of biomineralization and for the release of Ser.

Further aspects of the invention relates to artificial peptides having between 80-100% identity with the sequences of SEQ ID NO 1-8, such as peptides having 81, 82, 83, 84, 85, 86, 87, 88, 89, 90, 91, 92, 93, 94, 95, 97, 98 or 99% identity with the sequences of SEQ ID NO 1-8.

In preferred embodiments, the artificial peptides disclosed herein consist of SEQ ID NO 1-8, respectively.

A peptide according to the invention may further comprise N- and/or C-terminal tags comprising the amino acids His and/or Met. Met contains sulphur, which as previously explained facilitates binding to metal surfaces. His has a strong affinity for e.g. Ni and other metals. The use of these tags therefore has the advantage of enabling the peptides to attach to metal surfaces like titanium, zirconium, aluminium, tantalum, gold, surgical steel and nickel, or a metal oxide hydroxide and/or hydride surface etc. This is of great importance e.g. when a peptide of the invention is to be attached to a metal surface, such as when to be used to improve the biomineralization and/or osseointegration of a medical prosthetic device. The C- and/or N-terminal tags are also useful in the process of purification of produced peptides, as is well known to the skilled person. The use of an N-terminal and/or C-terminal tag also allows the peptide to be fully exposed, i.e. the tag is used for binding the peptide to a surface and the rest of the peptide is free for interactions with e.g. atoms, molecules, cells and tissue. The use of one tag in each end of a peptide may be useful during production of the peptide, allowing one end of the peptide being attached to a column during the purification of the peptide of interest from incomplete peptide products, while the other end of the peptide may be used for binding to a surface of interest. Consequently, one preferred embodiment of the invention relates to an artificial peptide as defined herein, further comprising an N-terminal and/or a C-terminal histidine tag. Such a tag may as previously mentioned, comprise methionine and/or histidine residues, which have been attached to an artificial peptide according to the invention. In a preferred embodiment, this tag comprises 3 or more residues, such as between 3-5 or 5-10 residues. A tag can comprise any amount of residues attached to an artificial peptide according to the invention, which still provides for a stable composition together with the artificial peptide according to the invention not affecting the secondary structure of the artificial peptide in a negative manner. Preferably this histidine tag consists of five histidine residues. In another preferred embodiment the artificial peptide comprises an N-terminal and/or C-terminal methionine tag, preferably consisting of five methionine residues. In another preferred embodiment, a peptide of the invention comprises a methionine tag in its C- or N-terminal end and a histidine tag in the other end.

Due to their shorter length, compared to natural proteins, the artificial peptides of the invention are easier to produce, e.g. by synthetic production or biosynthesis. The artificial peptides of the invention may be produced by any known method for production of peptides, such as synthetic production by chemical synthesis. Synthetic production also allows the use of amino acid analogues which may improve the stability of the peptides produced. The skilled person knows what methods are available for the synthesis of an amino acid sequence.

Preferably, bioproduction may be used as a method for producing the peptides. Bioproduction means the production of an amino acid sequence in a biological system, such as a cell culture or in microbial cells, e.g. bacterial cells. For bioproduction, it is necessary to construct the corresponding nucleic acid sequence encoding a specific amino acid sequence. The skilled person readily knows how to construct such a nucleic acid sequence once a specific amino acid sequence to be synthesized is determined upon, and how to produce the peptide and purify it from the system used to produce it (see e.g. Svensson J, Andersson C, Reseland J E, Lyngstadaas S P, Bulow L. Histidine tag fusion increase expression levels of active recombinant Amelogenin in *Escherichia coli*. Protein Expr Purif, 48; 134-41 (2006)).

The invention also relates to a pharmaceutical composition comprising an artificial peptide as defined herein or a combination of two or more artificial peptides as defined herein. Such a pharmaceutical composition optionally also comprises a pharmaceutically acceptable carrier, excipient and/or diluent. Pharmaceutical compositions in the present context also embrace cosmetic compositions as well as compositions belonging to the so-called grey area between pharmaceuticals and cosmetics, namely cosmeceuticals.

The pharmaceutical compositions may be in form of, e.g., solid, semi-solid or fluid compositions such as, e.g.,
  delivery devices, implants;
  powders, granules, granulates, capsules, agarose or chitosan beads, microspheres, nanoparticles;
  sprays, aerosols, inhalation devices;
  gels, hydrogels, pastes, ointments, creams, soaps, tooth paste;
  solutions, dispersions, suspensions, emulsions, mixtures, lotions, mouthwash, shampoos, enemas;
  kits containing e.g. two separate containers, wherein the first one of the containers comprises a peptide of the invention optionally admixed with other active drug substance(s) and/or pharmaceutically acceptable excipients, carriers and/or diluents and the second container comprises a suitable medium intended to be added to the first container before use in order to obtain a ready-to-use composition;

A composition comprising a peptide of the invention may be suitable for use during surgery, e.g. for local application (e.g. in the oral cavity) in the form of a gel, film or dry pellet, or as a rinsing solution or treatment with a paste or cream.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

The peptides of the invention may e.g. be applied on dentures, prostheses, implants, and to body cavities such as the oral, nasal and vaginal cavity.

Furthermore, application within the dental/odontologic area is also of great importance.

A pharmaceutically or cosmetically acceptable excipient, carrier and/or diluent is a substance which is substantially harmless to the individual to which the composition is to be administered. Such an excipient, carrier and/or diluent normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical composition is generally dependent on which kind of dosage form is chosen. In the following are given examples of suitable pharmaceutically acceptable excipients for use in different kinds of compositions for use according to the invention.

The choice of pharmaceutically acceptable excipient(s) in a composition for use according to the invention and the optimum concentration thereof cannot generally be predicted and must be determined on the basis of an experimental evaluation of the final composition.

However, a person skilled in the art of pharmaceutical formulation can find guidance in e.g., "Remington's Pharmaceutical Sciences", 18th Edition, Mack Publishing Company, Easton, 1990.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethylamine etc.

Suitable examples of preservatives for use in compositions according to the invention are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Other examples of gels for use in a composition according to the invention comprises hydrogels such as PEG (Poly Ethylene Glycol), dextransulphates, dextrose, heparansulphates, gelatins, or the like.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate, etc.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and chitosans such as, e.g., sodium alginate, etc.

The concentration of the artificial peptide in a pharmaceutical composition according to the invention will, as the skilled person readily understands, vary depending on the intended use of the composition. Typically, the concentration of the peptide in the pharmaceutical composition is about 0.01-1 mg/ml. The amount applied in vivo to a subject is typically about 10 ng-0.1 mg/cm$^2$, preferably about 1 μg/cm$^2$.

In one aspect, the invention relates to a surface comprising an artificial peptide according to the invention. Optionally this surface also comprises a mineral salt deposited thereon, such as calcium carbonate and/or calcium phosphate. In one preferred embodiment this surface is a metal and/or a metal oxide surface or a surface of a metal alloy and/or an oxide thereof. In one preferred embodiment said metal is titanium, zirconium, tantalum, aluminium, gold, surgical steel or nickel. In another preferred embodiment said metal oxide is titanium oxide, aluminium oxide, tantalum oxide or zirconium oxide. In yet another embodiment, a surface according to the invention is at least partially covered by an oxide of a metal or an alloy thereof comprising an artificial peptide as disclosed herein.

In yet another preferred embodiment, said surface is at least partially covered by a hydride of a metal or an alloy thereof, which comprises an artificial peptide according to the invention. The hydride layer formed on a surface according to the invention may comprise any hydride of a metal or an alloy thereof, or a mixture of several different hydrides of a metal or an alloy thereof. Examples of metals which may be used in the context of the present invention for forming a hydride layer are titanium, zirconium, hafnium or tantalum, or an alloy thereof. In the case of a surface of titanium or an alloy thereof the major part of the modified outer layer, i.e. more than 50%, is preferably constituted by titanium hydride. This titanium hydride layer may also comprise small amounts of other elements and/or hydrides thereof.

In one embodiment, the invention relates to a method for producing a hydride layer on a surface of a metal or an alloy thereof comprising an artificial peptide according to the invention. This may be performed either by coating a surface comprising a peptide with a layer of hydride, or by converting the surface into hydride. One preferred method for producing such a layer is to treat the implant with electrolysis. Metal hydride layers are further described in WO00/38753.

In yet another preferred embodiment, said surface comprises a layer of a corresponding hydroxide material selected from a metal hydroxide such as titanium hydroxide, zirconium hydroxide, tantalum hydroxide, hafnium hydroxide, niobium hydroxide and chromium and/or vanadium hydroxide, or an hydroxide of an alloy of a metal such as of titanium, zirconium, tantalum, hafnium, niobium or chromium, or any other metal as disclosed herein which surface comprises an artificial peptide according to the invention.

Furthermore, the invention also concerns a method for preparing a surface which is at least partially covered with a hydroxide layer of a metal or an alloy thereof, as disclosed herein, comprising an artificial peptide according to the invention, said method comprising subjecting surface parts of the metal material to an electrolysis treatment to form the layer of hydroxide material. Metal hydroxide layers are further described in WO03/08695.

It should be noted that the formation of a hydroxide, oxide and/or a hydride layer on a surface of a metal or an alloy thereof on a surface comprising an artificial peptide according to the invention depends on the conditions used during the electrolysis treatment. In general, an electrolysis treatment can be performed as disclosed herein for forming a hydroxide, hydride and/or oxide layer on a metal or an alloy thereof which incorporates an artificial peptide according to the invention. However, during acidic conditions, mainly a hydride layer will be formed on the surface, and during basic conditions mainly a hydroxide and/or oxide layer will be formed on a surface comprising a peptide according to the invention.

When the pH of the electrolyte is lower than the pI of the peptide, the net charge of the peptide will be positive. In an electrolytic cell the positively charged peptide will travel towards the negatively charged electrode where a hydride layer of a metal or an alloy thereof will be formed. If the pH is higher than the pI, the peptide will be negatively charged and will travel towards the positively charged electrode forming a hydroxide and/or an oxide layer on a surface of a metal or an alloy thereof. This shows that a peptide according to the invention may be used both in an acidic and in a basic environment, i.e. during hydration, hydroxidation and/or oxidation of a surface of a metal or an alloy thereof.

In yet another preferred embodiment said surface is a hydroxyl apatite, aragonite, bioglass, glass, polyurethane or polymeric medical prosthetic device surface. In another preferred embodiment said surface is a biological surface, as previously defined.

In one preferred embodiment the surface on which an artificial peptide of the invention is provided, is a medical prosthetic device surface, such as a metallic, metal oxide, or polymeric medical prosthetic device surface. As previously mentioned, such a medical prosthetic device surface may either comprise an artificial peptide of the invention, or optionally an artificial peptide and a mineral salt. Such medical prosthetic device surfaces are believed to induce and/or stimulate mineral precipitation and/or biomineralization on the medical prosthetic device surface when it is implanted in a subject. Thereby the osseointegration of the medical prosthetic device may be increased and the outcome of implantation of the device in a subject may thereby be improved. It is also possible to attach a peptide of the invention to a medical prosthetic device prior to implantation and grow cells, as exemplified above, thereon, which cells may then be biomineralized before implantation of the medical prosthetic device in a subject. In this case, biomineralized structures may be prepared on the surface of the medical prosthetic device. Biologically precipitated mineral has a different structure and other chemical properties than inorganically precipitated mineral and therefore has a better potential for functioning in biological systems. Without being limited to a particular theory, this improved functioning of the surfaces according to the invention in biological systems may be due to the charge of the surface as well as to the crystals forming the mineralized surface often being ordered in their structure, hence providing a more biocompatible environment than a synthetic structure. The cells may optionally be removed before implantation. Thereby a "bio-patterned", "bio-mimicking" or "bio-templating" surface may be prepared.

As previously defined, a medical prosthetic device in the present context relates to any device intended to be implanted into the body of a vertebrate animal, in particular a mammal, in particular a human. Medical prosthetic devices in the present context may be used to replace anatomy and/or restore any function of the body. Non-limiting examples of such devices are medical devices that replaces anatomy or restores a function of the body such as the femoral hip joint; the femoral head; acetabular cup; elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stapes, incus-stapes, malleus-incus, malleus-incus-stapes; cochlear implants;

orthopaedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices.

In another aspect the invention relates to a cell culture or a tissue comprising an artificial peptide according to the invention. Optionally this cell culture or tissue also comprises a mineral salt deposited therein, such as calcium carbonate and/or calcium phosphate. Said cell culture may e.g. comprise osteoblasts, osteocytes, osteoclasts, fibroblasts, stem cells, such as embryonic and mesenchymal stem cells, or progenitor, omnipotent, pluripotent and multipotent cells, muscle cells, adipocytes, cartilage or ligament cells. Said peptide and/or mineral salt is present in said cell culture and/or tissue in any biocompatible solution and/or in a natural solution, depending on if the environment for the biomineralization is in vitro or in vivo.

The artificial peptides of the invention find use in many situations where mineral precipitation and/or biomineralization is required. The invention therefore also relates to the use of an artificial peptide or pharmaceutical composition as defined herein for the induction and/or stimulation of mineral precipitation and/or biomineralization. An artificial peptide of the invention may be used for these purposes alone or in a combination of two or more peptides of the invention. The peptides of the invention may also be used together with natural proteins and/or peptides, such as amelogenins, inducing and/or stimulating mineralization and/or biomineralization. Hence one embodiment of the invention relates to a composition, such as a pharmaceutical composition, of an artificial peptide according to the present invention together with a biological polymer, such as but not limited to, amelogenin, fibrin, fibrinogen, laminin, collagen, polysaccharides, cellulose, etc.

One aspect of the invention relates to the use of the artificial peptides of the invention for the induction and/or stimulation of mineralization in e.g. cell cultures, tissues, onto surfaces and/or in solutions. In another aspect, the invention relates to such cell cultures, tissues, surfaces and/or solutions comprising an artificial peptide of the invention, as described above. Such cell cultures, tissues, surfaces and/or solutions will thereby have a mineralization and/or biomineralization inducing/stimulating activity. By providing a mineral salt to such a cell culture, tissue, surface and/or solution a mineralized structure will be obtained. Hence, for in vitro purposes a mineral salt is added, not being necessary in vivo due to the salt being available naturally in the organism.

As mentioned above, the artificial peptides of the invention may be used to induce mineral precipitation and/or biomineralization on a surface. Preferred examples of such surfaces are metal surfaces, such as titanium, zirconium, aluminium, tantalum, gold, surgical steel and nickel, or any other metal as disclosed herein and metal oxide hydroxide and/or hydride surfaces etc. Examples of metal oxide surfaces include, but are not limited to, titanium oxide, aluminium oxide, tantalum oxide or zirconium oxide. Other preferred surfaces include hydroxyl apatite, aragonite, bioglass, glass, polyurethane and polymeric medical prosthetic device surfaces. Preferred examples of surfaces also include medical prosthetic device surfaces, such as metallic, metal oxide, and polymeric medical prosthetic device surfaces. Also, particularly preferred surfaces include all kinds of biological surfaces, such as a tooth root surface, a dental enamel surface, a bone surface, a graft surface, a wound surface etc.

In another aspect of the invention an artificial peptide of the invention may be used for the induction and/or stimulation of mineralization of a cell culture for growth of tissues comprising cells for implantation, such as osteoblasts, osteocytes, osteoclasts, fibroblasts, stem cells, such as embryonic and mesenchymal stem cells, and progenitor, omnipotent, pluripotent and multipotent cells, muscle cells, adipocytes, cartilage or ligament cells. By also supplying a mineral salt as previously exemplified, the tissue grown may be mineralized before implantation. For this purpose an artificial peptide of the invention may be provided in solution in the cell culture medium and/or attached to the cell culture plate.

Another example of a surface according to the invention is a separation column surface. Such a surface may, together with an artificial peptide of the invention, be used for the separation of mineral and toxic metals from blood. Such a surface may also be used for the precipitation of -calcium and other minerals from liquids, such as infusion liquids.

In another aspect of the present invention, mineralization and/or biomineralization is induced and/or stimulated in the presence of a surface comprising an artificial peptide of the invention. This pertains to that the stimulation and or induction of mineralization and/or biomineralization may not only be induced on the surface itself, but also in the vicinity of the surface.

The present invention also relates to a method for providing a mineral precipitation and/or biomineralization inducing and/or stimulating surface comprising the steps of:
  b) providing a surface to be mineralised;
  c) providing an artificial peptide of the invention;
  d) contacting said peptide with said surface to provide said peptide on said surface.

This method may optionally also comprise the further the step of immersing said surface with said peptide in a solution comprising a mineral salt, such as a calcium phosphate and/or calcium carbonate salt. Preferred surfaces for the present invention have been described herein.

According to the present invention an artificial peptide may be used for the in vivo induction of bone, cartilage, cementum and/or dental tissue formation and/or regeneration.

In one preferred embodiment, step c) in the method above is performed using an electric current. In this case, preferably, the pH in an electrolyte comprising the peptide is below the pI of the peptide, the current below 20 V, the charge density between 0.1-1000 mA per square centimeters. Preferably, the temperature ranges from room temperature to 60 degrees Celcius. The pH may be adjusted with any acid, preferably acetic acid or another organic acid (tartaric acid, maleic acid, oxalic acid etc), but it is also possible to use HCl, HF and $H_3PO_4$. The electrolyte preferably comprises 0.005-1.0 M of a salt, preferably a calcium containing salt, but it is also possible to use NaCl or other salts.

The present invention also relates to a method for the in vivo induction and/or stimulation of biomineralization in the presence of a medical prosthetic device, such as on the medical prosthetic device or in the surrounding tissue, in a subject, comprising the steps of:
  a) providing an mineral precipitation and/or biomineralization inducing and/or stimulating medical prosthetic device surface produced by a method as described above;
  b) implanting said medical prosthetic device into said subject.

When the peptide according to the invention is used for inducing the biomineralization of a medical prosthetic device, different strategies may be used. Independently on the strategy chosen, the first step is always to cover the medical prosthetic device with the peptide, as described herein. The next step may then be to immerse the medical prosthetic device in a solution comprising at least one mineral salt for in vitro purposes, as previously described. Thereby the mineral deposits on the surface of the medical prosthetic device, providing a mineralized surface. The medical prosthetic device is thereafter implanted into a subject, where the artificial peptide and nucleation foci on the surface aid further mineral deposition in vivo. In an alternative approach, the medical prosthetic device is first covered by the peptide as previously mentioned. The medical prosthetic device is then implanted into a subject, where the peptide aids in mineral deposition on the medical prosthetic device surface.

Any suitable method known to the skilled person may be used for the attachment of a peptide according to the invention to a surface. An example of a preferred method for attachment of the peptides are described in e.g. Hayakawa et al (Hayakawa, T., Yoshinari, M., and Nemoto K. Direct attachment of fibronectin to tresyl chloride-activated titanium. J Biomed Mater Res A, 2003, 67 (2): 684-8) which describe the usage of tresyl chloride to attach a peptide to the surface of titanium implant. This method provides a limited release of the peptide from the surface and is used in example 5 in the experimental section. Another preferred method for attaching a peptide according to the invention to a surface is described in Imamura et al. (Imamura, K., Kawasaki, Y., Nagayasu, T., Sakiyama, T., and Nakanishi, K. Adsorption characteristics of oligopeptides composed of acidic and basic amino acids on titanium surface. J Biosci Bioeng, 2007, 103 (1): 7-12), disclosing the usage of the natural properties of the peptides to adhere to a titanium surface via their negatively charged carboxylic groups. This way of attaching a peptide according to the invention to a surface is illustrated in example 6 in the experimental section, and provides for a passive adsorption and release of the peptides into the tissues and/or cells surrounding the implant. As previously mentioned herein, a peptide according to the invention may also be attached to a surface by the use of N- and/or C-terminal tags comprising the amino acids His and/or Met.

There are several ways available to the skilled person to investigate if bone formation occurs on and/or around an implant with a peptide according to the invention. One way to detect the level of osteoblastic cell activity in a tissue with an implant is to detect the levels of the transcriptional factor runx2/Cbfa-1, which regulates the expression of bone extracellular matrix protein genes that encode for bone sialoprotein, osteocalcin and collage type I (Lian et al., Current Pharmaceutical Design, 2003, 9, 2677-2685). TRAP (Tartrate-Resistant Acid Phosphatase) expression may also be used to study bone resorption by osteoclastic cells in tissues, wherein a decrease in TRAP expression is indicative of a reduced bone resorption. Hence, the TRAP expression profile could give an indication of the presence of differentiated osteoclasts at the bone-implant interface (Minkin et al., "Role of the osteoclast at the bone-implant interface" Adv Dent Res 13:49-56, June, 1999).

LDH (Lactat dehydrogenase) activity may be used in the context of the present invention to investigate the biocompatibility of an implant with a peptide according to the invention, wherein a decreased activity indicates improved biocompatibility. LDH activity is present in the wound fluid, which is released from the inflamed bone tissue, and can be used as a marker of tissue necrosis at the bone-implant interface. (Michael Messieh, "Synovial Fluid levels of Lactate Dehydrogenase in Patients with Total Knee Arthroplasty, The Journal of Arthroplasty Vol. 11 No. 4, 1996; Michael Messieh, Levels of Lactate Dehydrogenase in Osteoarthritic and Failed Total Knee Joints, The Journal of Arthroplasty Vol. 11 No. 3, 1996)

In another aspect, the invention relates to a method for the in vivo induction and/or stimulation of biomineralization comprising the administration of an artificial peptide or a pharmaceutical composition comprising an artificial peptide as disclosed herein to a subject in need thereof. In order to achieve this, an artificial peptide of the invention is administered, alone or comprised in a pharmaceutical composition as disclosed herein, to the tissue of interest. The peptide may be administered in any suitable way depending on the intended use, such as by systemic and/or local injection and/or perfusion. When a peptide of the invention is administered to a tissue it may induce biomineralization and further bone formation. Examples of tissue of interest in the present context include bone, cartilage, cementum and teeth. Examples of conditions that may lead to bone fractures include, but are not limited to, bone resection, e.g. at trauma, tumours, cysts, and infections or inflammations, such as periodontitis, periimplantitis or ostitis. The peptide according to the invention may be administered to a subject in need thereof suffering from such a condition. The peptide, optionally with a pharmaceutically acceptable carrier, is preferably directly applied to the tissue. An artificial peptide of the invention may also be applied to a tissue or cell culture in vitro in order to induce mineral precipitation. For both the situation in vivo and in vitro, examples of cells that a peptide of the invention is of interest to be administered to are osteoblasts, osteocytes, osteoclasts, fibroblasts, stem cells, such as embryonic and mesenchymal stem cells, and progenitor, omnipotent, pluripotent and multipotent cells, muscle cells, adipocytes, cartilage and ligament cells.

Although not wishing to be bound by theory, one may envisage that a peptide of the invention may induce bone formation by the initiation of precipitation of calcium phosphate and/or the stimulation of cells involved in the formation of bone structures, such as osteoclasts or osteoblasts. Experiments performed by the inventors have shown that peptides comprising a consensus peptide of the invention may bind calcium. Also, experiments have demonstrated that a consensus sequence according to the invention may bind to a receptor involved in the biomineralization process.

A peptide of the invention and/or a pharmaceutical composition comprising such a peptide may be administered to a subject in need thereof by any suitable route depending on the tissue which the peptide is to be administered to, for example by topical (dermal), oral, buccal, nasal, aural, rectal or vaginal administration, or by administration to a body cavity such as, e.g., a tooth root, a tooth root canal or a bone fracture. Furthermore, a composition may be adapted to administration in connection with surgery, e.g. in connection with incision within the body. The peptides of the invention may also be administered via local injections, by application in a gel or via a medical device, such as a medical prosthetic device, e.g. a graft, scaffold or bioglass material. It is also possible to administer the peptides via alginate or citosan (slow release) beads, a toothpaste (which would enable remineralization of enamel together with fluoride), in a shampoo (with calcium, which would provide a hair strengthening and/or thickening composition), in a dental filling material (composite or in combination with root filling materials for induction of bone healing apically to the tooth). If administrated locally, as such or in a pharmaceutical composition comprising a peptide of the invention, into e.g. a fracture, periodontal defect, extraction alveolas or sinus lift procedure, the peptides of the invention may improve and/or speed up bone healing in the cases.

The peptides probably act by inducing mineral depositions that function as "seeds" for further bone formation including differentiation and maturation of bone cells.

For the administration for the treatment of osteoporosis the peptide may be encapsulated and delivered orally by ingestion, by the nasal cavity or lungs by inhalation or by injection into the blood, into the spinal fluid (spine fractures), into joints (to heal cartilage defects or degenerative changes to articulating surfaces) or intraperitoneally as a slow release depot.

In another aspect the invention relates to an artificial peptide as defined herein for use as a medicament. In particular the invention relates to the use of the artificial peptide and/or pharmaceutical composition for the preparation of a medicament for the induction of biomineralization. In particular the invention also relates to the use of an artificial peptide and/or a pharmaceutical composition comprising an artificial peptide for the preparation of a medicament for the formation and/or regeneration of bone. In a particular embodiment, the invention also relates to the use of an artificial peptide and/or a pharmaceutical composition comprising an artificial peptide for the preparation of a medicament for the formation and/or regeneration of bone cartilage, cementum and/or dental tissue. The peptides of the invention and/or pharmaceutical compositions comprising these peptides may also be used for the preparation of medicaments for the treatment of osteoporosis, fractures, periodontitis, traumas, bone metabolic syndrome, pulitis, dental apical lesions, etc.

The peptides of the invention and/or pharmaceutical compositions comprising these peptides may also be used for the preparation of a medicament for the healing of bone fractures.

In one aspect the invention also relates to an artificial peptide and/or a pharmaceutical composition comprising an artificial peptide as disclosed herein for use for the induction of biomineralization. For example an artificial peptide and/or a pharmaceutical composition comprising an artificial peptide according to the invention may be used for the preparation of a medicament for the formation and/or regeneration of bone cartilage, cementum and/or dental tissue.

In another aspect, the invention relates to an artificial peptide and/or a pharmaceutical composition comprising an artificial peptide as disclosed herein for use for the formation and/or regeneration of bone.

In yet another aspect, the invention relates to an artificial peptide and/or a pharmaceutical composition comprising an artificial peptide as disclosed herein for use for the healing of bone fractures.

The artificial peptides of the invention may also be used in combination with natural peptides inducing mineral precipitation and/or biomineralization and/or bone formation, such as amelogenins. It is also possible to use a combination of two or more peptides of the invention for the induction and/or stimulation of mineral precipitation, including biomineralization.

The artificial peptides of the invention may also be used for the fusion of two biomineralized structures, or the fusion of a biomineralized structure with another material. Examples of such materials include implantable biomaterials, such as titanium and steel, bioglass, calcium phosphates, apatite etc. Other examples include column material, filter materials etc.

EXPERIMENTAL SECTION

Example 1

A Peptide Based, Mineral-Inducing Coating on a Titanium Surface

Eight coin shaped implants with a diameter of 6.25 mm, was attached to an titanium electrode and submerged in an sterile electrolyte containing 0.5 M NaCl, adjusted to pH 8.0 by the use of 1.0 M NaOH, and a synthetic poly-proline peptide designed to stimulate nucleation of calcium phosphate crystals. The peptide, having a pI of 5.82, had the following sequence: PLV PSY PLV PSY PLV PSY PYP PLPP (SEQ ID NO:3), and was applied at a final concentration of 0.01 mg/ml in the electrolyte. The electrode was attached to the positive outlet of a power supply, and an electrical current of 10 Volts at 100 mA at a cell temperature of 40 degrees Celsius, was applied for eight hours. The electrolytic process produced a thin peptide coating onto the oxidized titanium surface visible as a greyish precipitation. After coating the titanium specimens were rinsed in sterile water and subsequently put into sterile glass containers where they were allowed to air-dry. Eight identical titanium specimens, treated identically as the test specimens with the exception that no peptides were added to the electrolyte, was produced as controls. After drying, the titanium specimens (peptide coated and controls) were submerged in 50 ml of a saturated solution of calcium phosphate at 50 degrees Celsius. The solution was then allowed to cool to room temperature and incubated at 25 degrees Celsius for 48 hours. The titanium specimens were then removed from the solution, rinsed briefly in sterile water and air-dried in a desiccator. When dry, the implants were directly analyzed by scanning electron microscopy (SEM) for quantitative and qualitative assessment of the number and nature of mineral precipitation foci present on their surfaces. The number of mineral forming units (mfu) on the surface directly corresponds to the number of mineral nucleation sites present on the surface during the experiments.

The results (Table 1) demonstrate that the titanium specimens that had their surfaces coated with the synthetic poly-proline peptide had a significantly ($p<0.01$) increased number of mineral deposition foci. The deposited mineral had a high content of Calcium and Phosphor (element analysis by SEM-EDX) indicating that the depositions were all calcium phosphate. This is a strong indication that the synthetic peptide used here positively influence the formation of bone mineral deposition onto titanium surfaces.

TABLE 1

Number of mineral forming units (mfu) per square mm titanium surface assessed by SEM. Values above 10,000 are recorded as "Confluent".

| Specimen | Controls (n = 8) | Peptide coated (n = 8) |
| --- | --- | --- |
| 1 | 1225 mfu | 8100 mfu |
| 2 | 1936 mfu | Confluent |
| 3 | 2704 mfu | Confluent |
| 4 | 1369 mfu | 5625 mfu |
| 5 | 3844 mfu | Confluent |
| 6 | 5184 mfu | 7744 mfu |
| 7 | 1444 mfu | Confluent |
| 8 | 3249 mfu | 9025 mfu |
| Mean values | 2619 mfu | >8812 mfu |

Example 2

A Synthetic Poly-Proline Peptide Coating Promoting Mineral Precipitation on a Medical Titanium Implant Surface A layer of a synthetic poly-proline peptide with the sequence PLV PSQ PLV PSQ PLV PSQ PQP PLPP (SEQ ID NO:4) and a pI of 5.55 that has the potential to act as a biological nucleator of mineral formation was used for coating medical implants made of titanium. The peptide was coated onto eight sterile dental implants with a total surface area of about 1 square centimeter using a galvanic cell. The electrolyte used in was 1M NaCl in sterile water with pH adjusted to pH 2 by means of HCl, and the initial concentration of the synthetic poly-proline was 0.1 mg per ml electrolyte. A voltage of 10 volts at a current density of 1 mA/cm$^2$ was used. At this pH the poly-proline peptide is negatively charged and will migrate towards the positive electrode to which the implants were attached. The process was run at ambient temperature. Electrolysis was allowed to progress for 4 hours after which the titanium implants were removed from the galvanic cell, rinsed in sterile water and allowed to air-dry in a desiccator. Eight control implants were produced in an identical setup, but without the synthetic poly-proline peptide. After drying, the titanium implants (peptide coated and controls) were submerged in 50 ml of a saturated solution of calcium phosphate at 50 degrees Celsius. The solution was then allowed to cool to room temperature and incubated at 25 degrees Celsius for 24 hours. The titanium specimens were then removed from the solution, rinsed briefly in sterile water and air-dried in a desiccator. When dry, the implants were directly analyzed by scanning electron microscopy (SEM) for quantitative and qualitative assessment of the number and nature of mineral precipitation foci present on their surfaces. The number of mineral forming units (mfu) on the surface directly corresponds to the number of mineral nucleation sites present on the surface during the experiments.

The results (Table 2) demonstrate that the titanium implants that had their surfaces coated with the synthetic poly-proline peptide had a significantly ($p<0.01$) increased number of mineral deposition foci. The deposited mineral had a high content of Calcium and Phosphor (element analysis by SEM-EDX) indicating that the depositions were all calcium phosphate. Metal implant surfaces that has the ability to induce and promote nucleation and deposition of bone mineral (calcium phosphates) onto their surfaces are likely to perform better clinically than other implants. An increased rate of bone mineral deposition onto the implant surface is believed to speed up osseointegration of the implant and stimulate the healing of the surrounding bone tissue. A proper osseointegration is regarded the hallmark for successful clinical outcomes of orthopedic and dental implant treatments.

TABLE 2

Number of mineral forming units (mfu) per square mm on implant surfaces.

| Implants | Controls (n = 8) | Peptide coated (n = 8) |
| --- | --- | --- |
| 1 | 924 mfu | 7220 mfu |
| 2 | 930 mfu | 8905 mfu |
| 3 | 712 mfu | 6775 mfu |
| 4 | 1278 mfu | 6566 mfu |
| 5 | 1876 mfu | 5788 mfu |
| 6 | 2020 mfu | 8772 mfu |
| 7 | 1383 mfu | 7543 mfu |
| 8 | 1123 mfu | 8031 mfu |
| Mean values | 1281 mfu | 7450 mfu |

Example 3

Testing of Titanium Implants Having their Biocompatibility Improved by Electrolytic Deposition of a Consensus Peptide in the Surface Eight coin shaped, machined implants with a diameter of 6.25 mm, will be attached to a titanium electrode and submerged in an sterile electrolyte containing 0.5 M NaCl adjusted to pH 8.0 by the use of 1.0 M NaOH, and containing 0.1 mg/ml of an artificial peptide of the invention (pI<8.0, peptides are ampholytes having a net negative charge when the pH is higher than the pI of the molecule). The electrode will be attached to the positive outlet of a power supply, using a charge density of 1 mA/cm$^2$. The electrolytic process will produce a thin layer of titanium oxide containing the consensus peptide on the implant surfaces. The process will be allowed to continue for two hours at room temperature. After electrolysis the implants will be cleaned in sterile water and subsequently put into sterile glass containers where they will be allowed to air-dry. For control eight parallel implants will be treated in the same way, but in an electrolyte without the consensus peptide.

The implants with consensus peptide coated surfaces (n=8) and controls (n=8) will be placed in calibrated cortical bone defects in the tibia of rabbits (New Zealand White). A small central fenestration into the bone marrow beneath each implant will be made to allow for migration of osteogenic cells to the implant surfaces. The methods used will all be according to a standardized and validated model established for the study of bone attachment to titanium implant surfaces (Ronold, H. J. and Ellingsen, J. E. The use of a coin shaped implant for direct in situ measurement of attachment strength for osseointegrating biomaterial surfaces. Biomaterials 23; 2201-2209 (2002)). Each rabbit will receive four implants, two in each tibia bone. Location of test and control implants will be randomized and the operator will be blinded. At six weeks after implantation the rabbits will be sacrificed and the tibia bones with the implants attached will be excised. Directly after excising the tibia bone will be fixed in a specially designed jig, and the implant will be detached using a calibrated pull-out procedure measuring the strength of the bonding between the implant and the bone. The force needed to detach the implants will be recorded in Newton (N).

The results are expected to demonstrate that the titanium implants that had surfaces coated by a consensus peptide were more strongly attached to cortical bone than the untreated control implants after six weeks of healing. This result will be clinically important as early bone attachment is a sign of reduced bone healing time. This is important for successful clinical outcomes of "early loading" strategies in orthopedic and dental implant treatments.

Example 4

Preparation of a Osteoinductive Titanium Implant Surface Containing a Consensus Peptide Eight coin shaped, machined implants with a diameter of 6.25 mm, will be attached to a titanium electrode and submerged in an sterile electrolyte containing 0.5 M NaCl, adjusted to pH 5.0 by the use of 1.0 M HCl, and containing 0.01 mg/ml of an artificial peptide according to the invention (pI>5.0, peptides are ampholytes having a net positive charge when the pH is lower than the pI of the molecule). The electrode will be attached to the negative outlet of a power supply, using a net charge density at the implant surface of 1 mA/cm$^2$. The process will be allowed to run for 1 hour at 50 degrees Celsius. The electrolytic process will produce implants surfaces with a thin coating with the consensus peptide. After electrolysis the implants will be rinsed in sterile water and subsequently put into sterile glass containers where they will be allowed to air-dry. Eight implants will be treated the same way, but without the consensus peptide, and included as controls.

The titanium implants with peptide modified surfaces (n=8) and controls (n=8) will be placed in calibrated cortical bone defects in the tibia of rabbits (New Zealand White). A small central fenestration into the bone marrow beneath each implant will be made to allow for migration of osteogenic cells to the implant surfaces. The methods used will all be according to a standardized and validated model established for the study of bone attachment to titanium implant surfaces (Ronold, H. J. and Ellingsen, J. E. The use of a coin shaped implant for direct in situ measurement of attachment strength for osseointegrating biomaterial surfaces. Biomaterials 23; 2201-2209 (2002)). Each rabbit will receive four implants, two in each tibia bone. Location of test and control implants were randomized and the operator will be blinded. At four weeks after implantation the rabbits were sacrificed and the tibia bones with the implants attached will be excised. Directly after excising the tibia bone will be fixed in a specially designed jig, and the implant will be detached using a calibrated pull-out procedure measuring the strength of the bonding between the implant and the bone. The force needed to detach the implants will be recorded in Newton (N).

The results are expected to demonstrate that the titanium implants that had surfaces modified by electrolytic incorporation of a consensus peptide more strongly attached to cortical bone than the control implants after four weeks of healing. This result will be clinically important as early bone attachment is a sign of reduced bone healing time. This is important for successful clinical outcomes of "early loading" strategies in orthopedic and dental implant treatments.

Example 5

Experiments performed with Peptide: PLV PSQ PLV PSQ PLV PSQ PQP PLP P (SEQ ID NO:4)
1. Materials and Methods
1. 1 Titanium Coins Commercially pure (cp) machined titanium implants with a diameter of 6.25 mm and a height of 1.95 mm were cleaned and sterilized before use. Briefly, implants were washed together in a glass beaker with deionised water for 30 s, then with 70% ethanol for 30 s, and then with ultrasonic bath at 40° C. for 5 min in deionised water. The implants were subsequently placed in 40% NaOH solution in a water bath of 40° C. for 10 min, sonicated in deionised water for 5 min, and then washed with deionised water until the pH reached 6. Afterwards the implants were sonicated in deionised water at 50° C. for 5 min, placed in 50% HNO3 solution at 50° C. for 10 min, and sonicated in deionised water for another 5 min. The implants were washed with deionised water until reached pH=6 and were stored in 70% ethanol. Before use, the coins were rinsed with water, rinsed with ethanol, sonicated for 5 min at room temperature and rinsed with deionised water. The titanium coins were then sterilised by autoclaving at 121° C. for 15 min.
1. 2 Preparation of Peptide Solution The peptide (PLV PSQ PLV PSQ PLV PSQ PQP PLP P) (SEQ ID NO 4) was dissolved in phosphate-buffered saline (PBS) with pH=7.4 at a concentration of 20 mg/ml. This solution was further dissolved in PBS to a final concentration of 0.1 mg/ml.
1. 3. Activation of Titanium Implants with Tresyl Chloride and Coupling with Peptide The surface of the machined titanium implant was first covered with 10 µl of tresyl chloride (2,2,2-trifluoroethane-sulfonyl chloride) and incubated at 37° C. for 2 days. Then, the tresylated titanium implant was washed with water, water-acetone (50:50), acetone, and dried in a desiccator.

Peptide solution (10 µl, 0.1 mg/ml) was applied to the surface of the titanium implant and incubated for 24 h at 37° C., then rinsed with water. Finally, implants were dried in a desiccator, packed and stored at 4° C.

Control implants were activated with tresyl chloride but no peptide was added subsequently. Method used for binding peptide to titanium implants with tresyl chloride was adapted from (Hayakawa et al, 2003).
1.4 Animal Study Six New Zealand White female rabbits, 6 months old and a weight of 3.0-3.5 kg, were used in this study (ESF ProdukterEstuna AB, Norrtälje, Sweden).

The implants with consensus peptide coated surfaces (n=12) and controls (n=12) were placed in calibrated cortical bone defects in the tibia of rabbits (New Zealand White). A small central fenestration into the bone marrow beneath each implant was made to allow for migration of osteogenic cells to the implant surfaces. The methods used were all according to a standardized and validated model established for the study of bone attachment to titanium implant surfaces (Rønold and Ellingsen, 2002). Each rabbit received four implants, two in each tibia bone. Location of test and control implants was randomized and the operator was blinded. At four weeks after implantation the rabbits were sacrificed and the tibia bones with the implants attached were excised. Directly after excising the tibia bone was fixed in a specially designed jig, and the implants were detached using a calibrated pull-out procedure. The implants were then directly transferred to a sterile tube and processed for RNA and protein extraction, for the analysis of expression of bone markers and necrosis.
1.5. In Vivo Gene Expression of Bone Markers: Runx2, Osteocalcin and TRAP.

Figure 2:
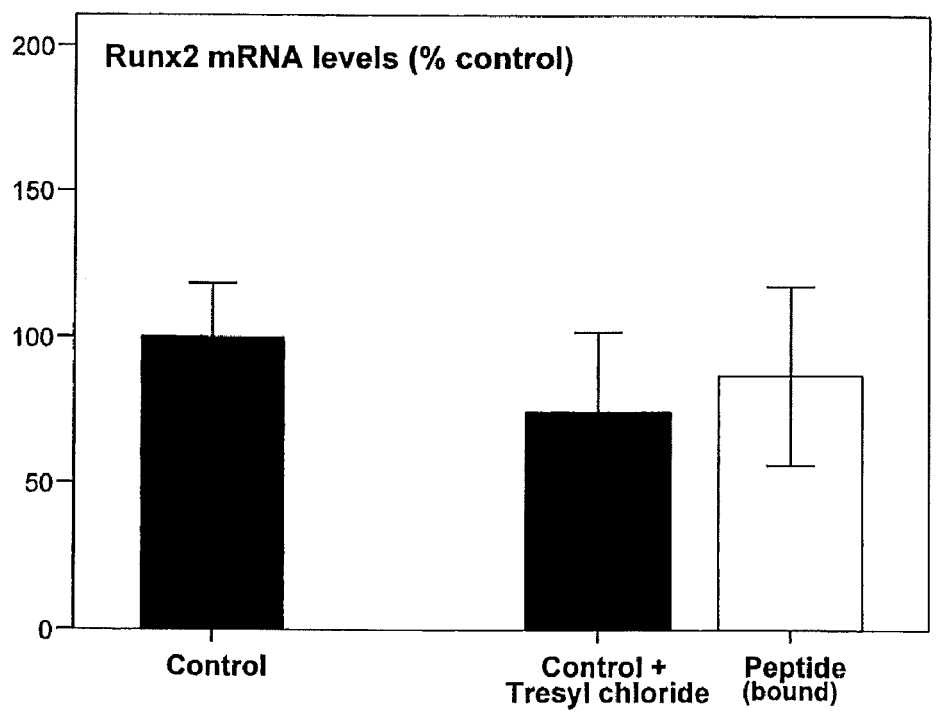
FIG. 2. Runx2 gene expression in the peri-implant bone tissue attached to the modified titanium implants (Example 5).
Figure 3:
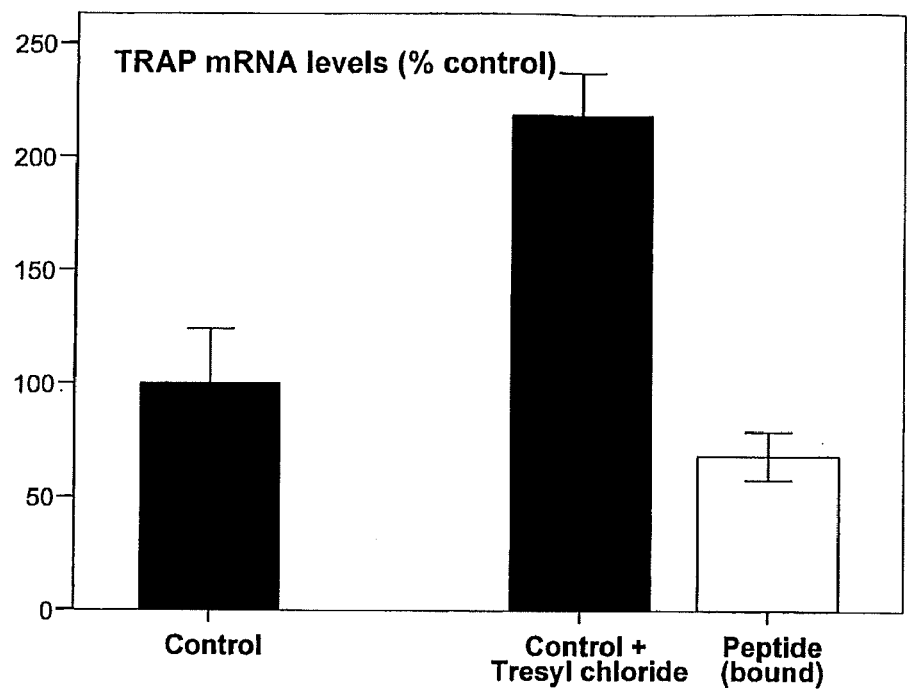
FIG. 3. TRAP gene expression in the peri-implant bone tissue attached to the modified titanium implants (Example 5)
Figure 4:
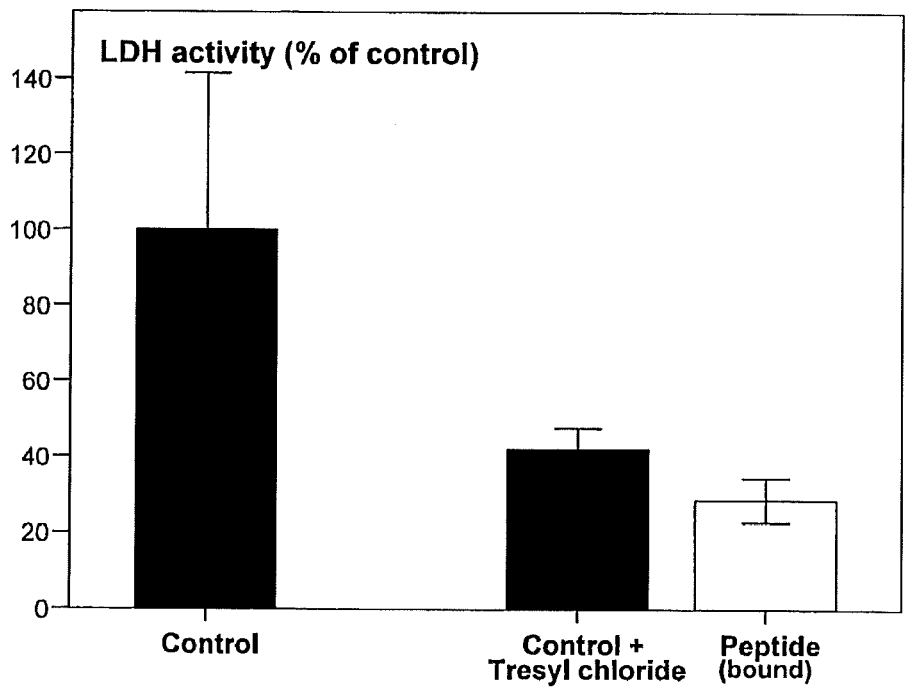
FIG. 4. LDH activity measured in the wound fluid collected from the implant site after 4 weeks of healing time (Example 5).

Gene expression of runx2, osteocalcin and TRAP was studied using real-time RT-PCR as an indication of bone formation (runx2, osteocalcin) or bone resorption (TRAP) in the peri-implant bone tissue attached to the surface of the different implants.
1.6 Wound Fluid Analyses: LDH Activity and Total Protein LDH activity and total protein was analysed in the wound fluid collected from the implant site following a 4 week healing period. The release of LDH is a sensitive marker for tissue necrosis (Williams et al, 1983) and thus the biocompatibility of the implants. The amount of total, protein was used to normalize for errors caused by differences in the number of bone cells on the detached implants.
2. Conclusion The implants coated with the consensus peptide showed a significant increase in osteocalcin expression indicating that osteoblastic cell activity was improved in these samples. Moreover, a decrease in TRAP expression was observed suggesting that bone resorption by osteoclastic cells was significantly reduced in these samples. Together these effects add up to a net increase in bone formation adjacent to implants coated with the consensus peptide. Moreover, the decrease in LDH activity in the periimplant tissue indicates that the presence of the consensus peptide significantly improved the biocompatibility of the titanium implant. These results are illustrated in FIGS. 1-4.

Example 6

Experiments performed with Peptide: PLV PSQ PLV PSQ PLV PSQ PQP PLP P (SEQ ID NO 4)

1. Materials and Methods
1. 1 Titanium Coins

Commercially pure (cp) machined titanium implants with a diameter of 6.25 mm and a height of 1.95 mm were cleaned and sterilized before use. Briefly, implants were washed together in a glass beaker with deionised water for 30 s, then with 70% ethanol for 30 s, and then with ultrasonic bath at 40° C. for 5 min in deionised water. The implants were subsequently placed in 40% NaOH solution in a water bath of 40° C. for 10 min, sonicated in deionised water for 5 min, and then washed with deionised water until the pH reached 6. Afterwards the implants were sonicated in deionised water at 50° C. for 5 min, placed in 50% $HNO_3$ solution at 50° C. for 10 min, and sonicated in deionised water for another 5 min. The implants were washed with deionised water until reached pH=6 and were stored in 70% ethanol. Before use, the coins were rinsed with water, rinsed with ethanol, sonicated for 5 min at room temperature and rinsed with deionised water. The titanium coins were then sterilised by autoclaving at 121° C. for 15 min.

1. 2 Preparation of Peptide Solution

The peptide (PLV PSQ PLV PSQ PLV PSQ PQP PLP P) (SEQ ID NO 4) was dissolved in phosphate-buffered saline (PBS) with pH=7.4 at a concentration of 20 mg/ml. This solution was further dissolved in PBS to a final concentration of 0.1 mg/ml.

1.3 Adsorption of Peptide to Titanium Implants (Physical Adsorption)

Peptides can be physically adsorbed onto a titanium surface, as an alternative method for covalent binding. Negatively charged carboxylic groups show a strong affinity for metal oxide surfaces and can therefore directly interact with the titanium surface (Imamura et al, 2007). Peptide solution (10 μl, 0.1 mg/ml) was applied to the surface of the titanium implant and incubated for 24 h at 37° C. After 24 h, titanium implants were rinsed and packed with the same method as described above. Control implants were treated with 10 μl of PBS without adding peptide.

1.4 Animal Study

Six New Zealand White female rabbits, 6 months old and a weight of 3.0-3.5 kg, were used in this study (ESF ProdukterEstuna AB, Norrtälje, Sweden).

The implants with consensus peptide coated surfaces (n=12) and controls (n=12) were placed in calibrated cortical bone defects in the tibia of rabbits (New Zealand White). A small central fenestration into the bone marrow beneath each implant was made to allow for migration of osteogenic cells to the implant surfaces. The methods used were all according to a standardized and validated model established for the study of bone attachment to titanium implant surfaces (Rønold and Ellingsen, 2002). Each rabbit received four implants, two in each tibia bone. Location of test and control implants was randomized and the operator was blinded. At four weeks after implantation the rabbits were sacrificed and the tibia bones with the implants attached were excised. Directly after excising the tibia bone was fixed in a specially designed jig, and the implants were detached using a calibrated pull-out procedure. The implants were then directly transferred to a sterile tube and processed for RNA and protein extraction, for the analysis of expression of bone markers and necrosis.

1.5. In Vivo Gene Expression of Bone Markers: Runx2, Osteocalcin and TRAP.

Gene expression of runx2, osteocalcin and TRAP was studied using real-time RT-PCR as an indication of bone formation (runx2, osteocalcin) or bone resorbtion (TRAP) in the peri-implant bone tissue attached to the surface of the different groups of implants.

1.6 Wound Fluid Analyses: LDH Activity and Total Protein

LDH activity and total protein was analysed in the wound fluid collected from the implant site following a 4 week healing period. The release of LDH is a sensitive marker for tissue necrosis [Williams et al, 1983] and thus the biocompatibility of the implants. The amount of total protein was used to normalize for errors caused by differences in the number of bone cells on the detached implants.

2. Conclusion

Figure 5:
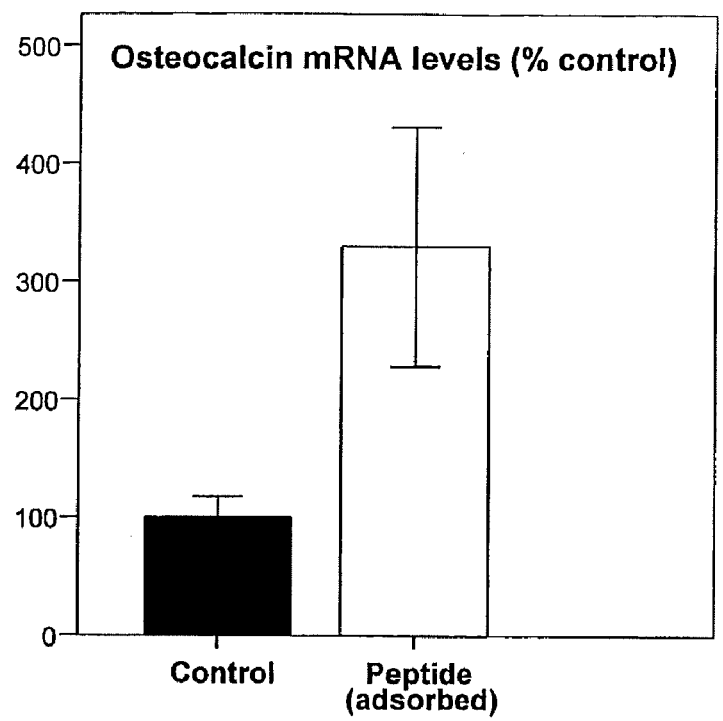
FIG. 5. Osteocalcin gene expression in the peri-implant bone tissue attached to the modified titanium implants (Example 6).
Figure 6:
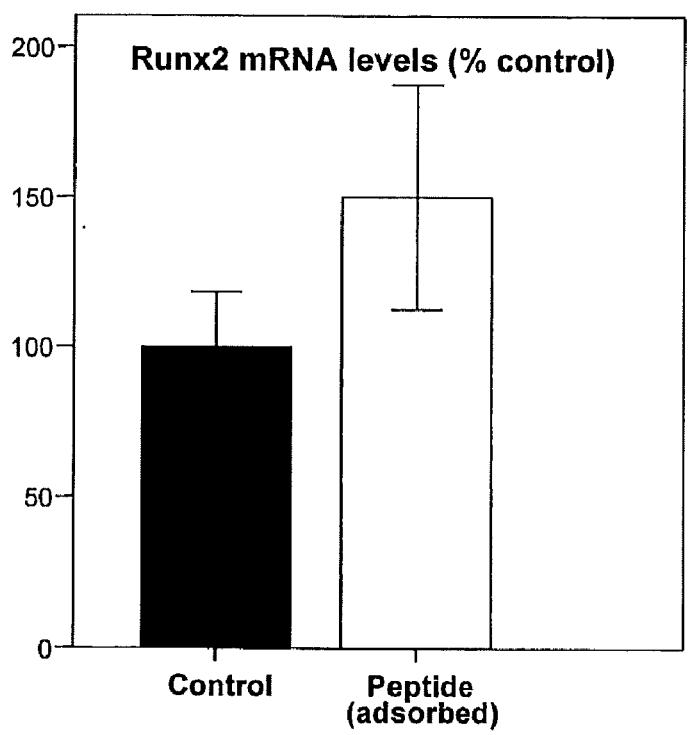
FIG. 6. Runx2 gene expression in the peri-implant bone tissue attached to the modified titanium implants (Example 6).
Figure 7:
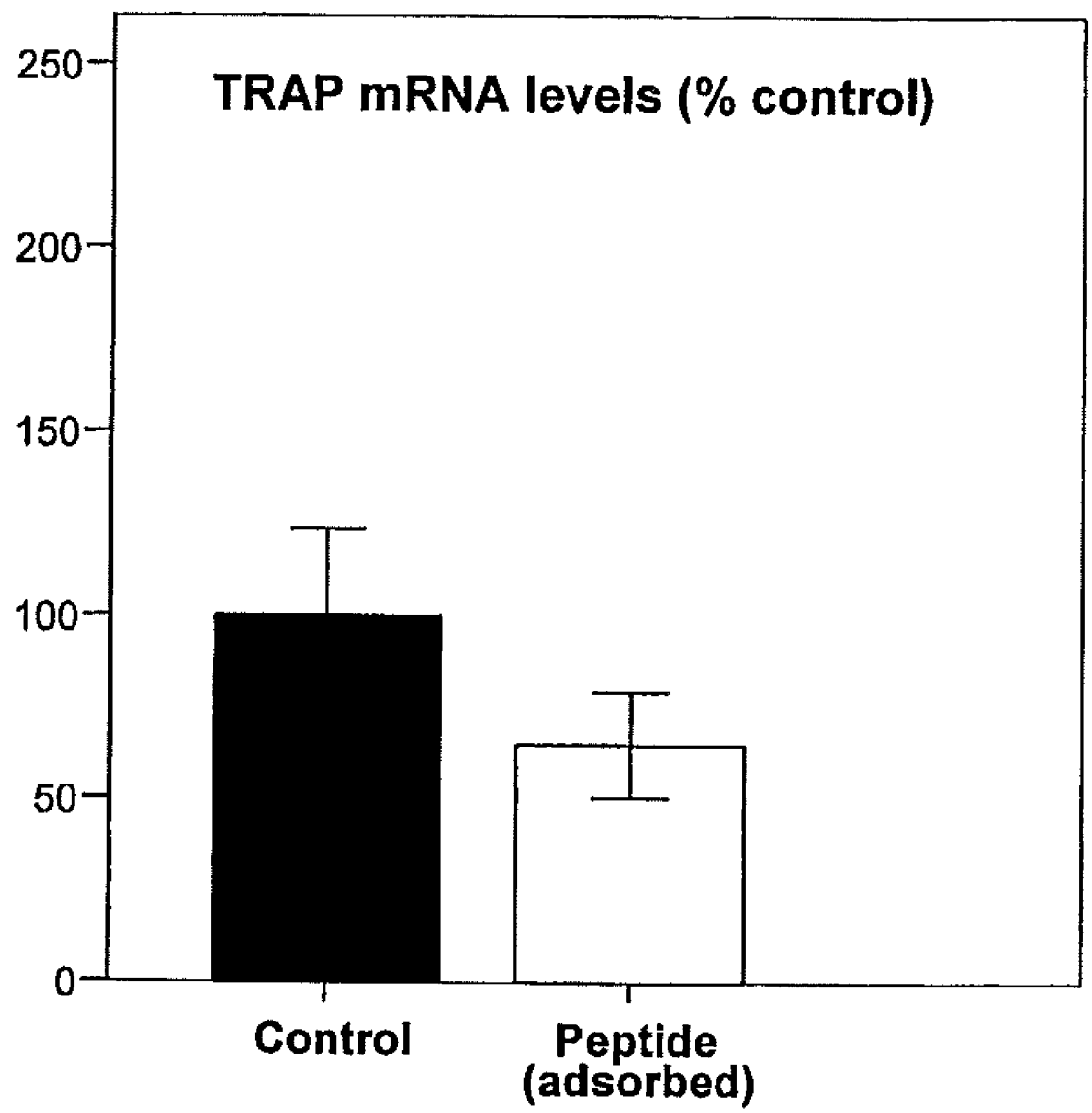
FIG. 7. TRAP gene expression in the peri-implant bone tissue attached to the modified titanium implants (Example 6).
Figure 8:
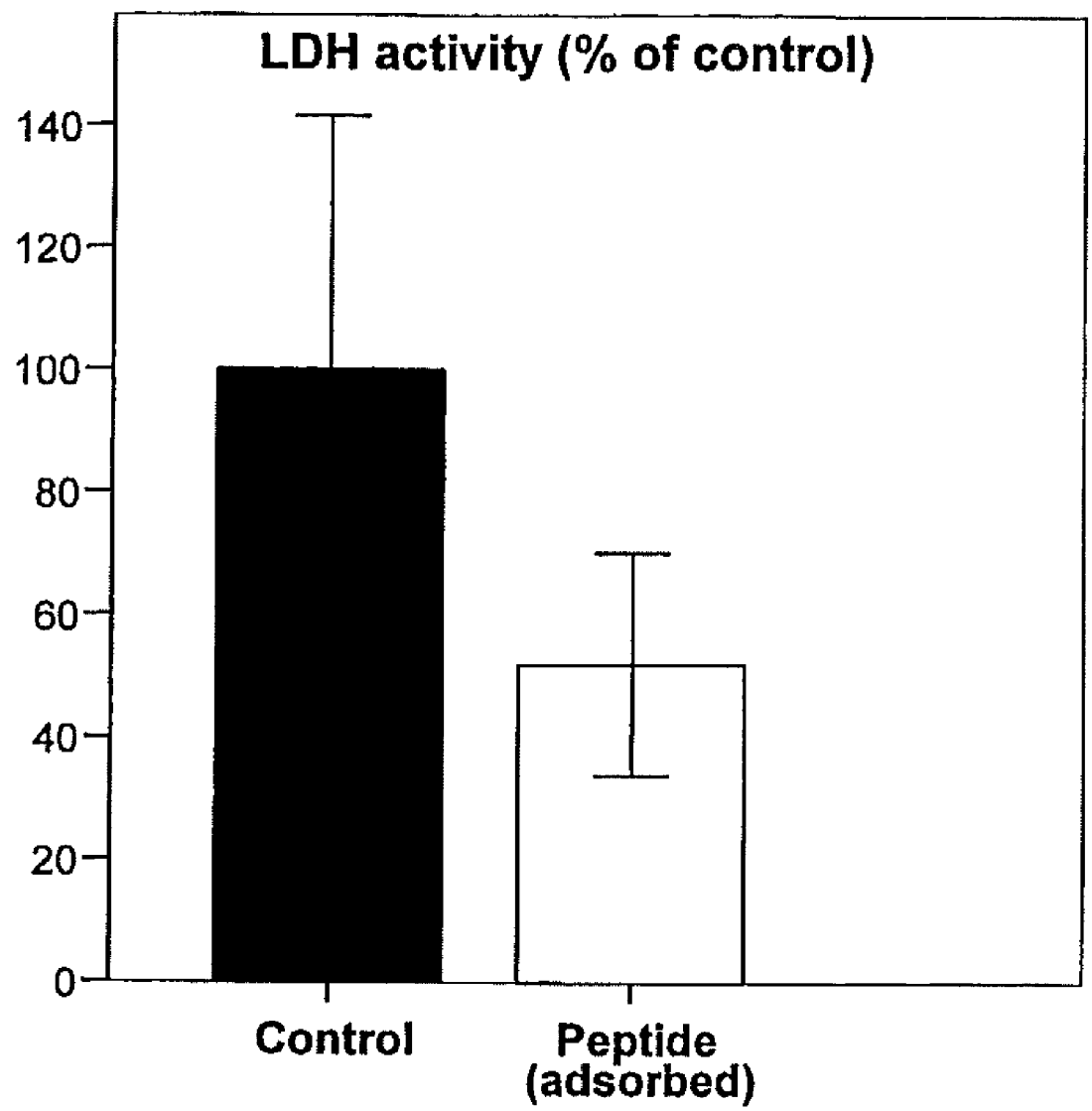
FIG. 8. LDH activity measured in the wound fluid collected from the implant site after 4 weeks of healing time (Example 6).

The implants coated with the consensus peptide showed a significant increase in the expression of the pro-osteogenic markers Osteocalcin and Runx2, strongly indicating that osteoblastic cell activity was improved in these samples. Moreover, a decrease in TRAP expression was observed, suggesting that bone resorption by osteoclastic cells was significantly reduced in these samples. Together these effects add up to a significant net increase in bone formation in the tissue adjacent to implants coated with the consensus peptide. Moreover, the observed decrease in LDH activity in the peri-implant tissue indicates that the consensus peptide significantly improved the biocompatibility of the titanium implants. The results of this study are shown in FIGS. 5-8.

REFERENCES

Brånemark et al. "Osseointegrated medical prosthetic devices in the treatment of the edentulous jaw, Experience from a 10-year period", Almqvist & Wiksell International, Stockholm, Sweden Svensson J, Andersson C, Reseland J E, Lyngstadaas S P, Bulow L. "Histidine tag fusion increase expression levels of active recombinant Amelogenin in *Escherichia coli.*", Protein Expr Purif, 48; 134-41 (2006)

Hayakawa, T., Yoshinari, M., and Nemoto K. "Direct attachment of fibronectin to tresyl chloride-activated titanium", J Biomed Mater Res A, 2003, 67 (2): 684-8

Imamura, K., Kawasaki, Y., Nagayasu, T., Sakiyama, T., and Nakanishi, K. "Adsorption characteristics of oligopeptides composed of acidic and basic amino acids on titanium surface." J Biosci Bioeng, 2007, 103 (1): 7-12.

Lian et al., Current Pharmaceutical Design, 2003, 9, 2677-2685

Minkin et al., "Role of the osteoclast at the bone-implant interface" Adv Dent Res 13:49-56, June, 1999

Michael Messieh, "Synovial Fluid levels of Lactate Dehydrogenase in Patients with Total Knee Arthroplasty, The Journal of Arthroplasty Vol. 11 No. 4, 1996

Michael Messieh, "Levels of Lactate Dehydrogenase in Osteoarthritic and Failed Total Knee Joints", The Journal of Arthroplasty Vol. 11, No. 3, 1996

Ronold, H. J. and Ellingsen, J. E. "The use of a coin shaped implant for direct in situ measurement of attachment strength for osseointegrating biomaterial surfaces." Biomaterials 23; 2201-2209 (2002)

Williams D L, Marks V. Biochemistry in Clinical Practice. London: William Heineman Medical Books; 1983.

The invention claimed is:

1. An artificial peptide comprising the amino acid sequence of Z-X-X-Z-Y-Y-Y-Z-X-X-Z-Y-Y-Z-X-X-Z-X-Z-Y-Y-Y-Y-Y-Z-Y-Y-Y-Y-Y-Z-X-X-Z-X-Z-Y-Y-Y-Z-Y-Y-Z-Y-Z-X-X-Z-Y-Z-Y-Y-Z-X-X-Z-Y-Y-Z-X-X-Z-Y-Y-Z-X-X-Z-Y-Z-Z-X-Z-Z-X-X-X-X-X-X-X-Z-X-X-Z-X-X-X-X (SEQ ID NO:1), wherein
   a) Z is Pro;
   b) X is an amino acid selected from the group consisting of Ala, Ile, Leu, Met, Phe, Trp, and Val; and
   c) Y is an amino acid selected from the group consisting of Asn, Cys, Gln, Ser, Thr, and Tyr.

2. An artificial peptide according to claim 1 further comprising an N-terminal and/or C-terminal histidine tag.

3. An artificial peptide according to claim 2 comprising one histidine tag and one methionine tag.

4. An artificial peptide according to claim 1 further comprising an N-terminal and/or C-terminal methionine tag.

5. A pharmaceutical composition comprising one or more artificial peptides according to claim 1 and optionally a pharmaceutically acceptable carrier, excipient and/or diluent.

6. An artificial peptide comprising the amino acid sequence of SEQ ID NO:3, SEQ ID NO:4, SEQ ID NO:5, SEQ ID NO:6, SEQ ID NO:7, or SEQ ID NO:8.

7. A metal, metal oxide, metal hydroxide, metal hydride, hydroxyl apatite, aragonite, bioglass, glass, polyurethane, polymeric medical prosthetic device, medical prosthetic device, biological surface, and combinations thereof comprising an artificial peptide according to claim 1 and optionally comprising a mineral salt deposited thereon.

8. A method for inducing and/or stimulating mineral precipitation and/or biomineralization in a cell culture, in a tissue, onto a surface, and/or in a solution, comprising:
   administering to said cell culture, tissue, surface, and/or solution a pharmaceutical composition comprising a peptide according to claim 1.

9. The method according to claim 8, wherein said surface is a metal, metal oxide, metal hydroxide, metal hydride, hydroxyl apatite, aragonite, bioglass, glass, polyurethane, polymeric medical prosthetic device, medical prosthetic device, biological surface, and combinations thereof.

10. A method for providing a mineral precipitation and/or biomineralization inducing and/or stimulating surface comprising the steps of:
   a) providing a surface to be mineralised;
   b) providing a peptide according to claim 1; and
   c) contacting said peptide with said surface to provide said peptide on said surface.

11. A method according to claim 9, further comprising the step of immersing said surface with said peptide in a solution further comprising a mineral salt, such as calcium phosphate and/or calcium carbonate.

12. A method according to claim 9, wherein step c) is performed using an electric current.

13. A method according to claim 10, wherein said surface is a metal, metal oxide, metal hydroxide, metal hydride, hydroxyl apatite, aragonite, bioglass, glass, polyurethane, polymeric medical prosthetic device, medical prosthetic device surface, and combinations thereof.

14. A method for the in vivo induction and/or stimulation of biomineralization of a medical prosthetic device in a subject comprising the steps of:
   a) providing a medical prosthetic device surface for induction of mineral precipitation and/or biomineralization produced by a method according to claim 10; and
   b) implanting said medical prosthetic device into said subject.

15. A method for the in vivo induction of bone, cartilage, cementum and/or dental tissue formation comprising the administration of a pharmaceutical composition comprising a peptide according to claim 1, to a subject in need thereof.

16. A method for fusing two biomineralized structures or for fusing a biomineralized structure and another material, comprising:
   contacting an artificial peptide according to claim 1 with said two biomineralized structures or said biomineralized structure and other material.

17. An artificial peptide comprising the amino acid sequence of Z-X-X-Z-Y-Y-Z-X-X-Z-Y-Y-Z-X-X-Z-Y-Y-Z-Y-Z-Z-X-Z-Z (SEQ ID NO:2), wherein
   a) Z is Pro;
   b) X is an amino acid selected from the group consisting of Ala, Ile, Leu, Met, Phe, Trp, and Val;
   c) Y is an amino acid selected from the group consisting of Asn, Cys, Gln, Ser, Thr, and Tyr.

18. A method for the in vivo induction and/or stimulation of biomineralization comprising the administration of an artificial peptide according to claim 1, claim 17, or claim 6 or a pharmaceutical composition according to claim 5, to a subject in need thereof.

* * * * *

UNITED STATES PATENT AND TRADEMARK OFFICE
CERTIFICATE OF CORRECTION

PATENT NO. : 8,367,602 B2  Page 1 of 1
APPLICATION NO. : 12/520651
DATED : February 5, 2013
INVENTOR(S) : Lyngstadaas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 257 days.

Signed and Sealed this
First Day of September, 2015

Michelle K. Lee
*Director of the United States Patent and Trademark Office*